(12) United States Patent
McKinnis et al.

(10) Patent No.: US 10,034,655 B2
(45) Date of Patent: Jul. 31, 2018

(54) TEMPORAL ECHOGENIC MARKERS

(71) Applicant: Muffin Incorporated, West Lafayette, IN (US)

(72) Inventors: Peter S. McKinnis, West Lafayette, IN (US); Yun Zhou, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 194 days.

(21) Appl. No.: 14/170,705

(22) Filed: Feb. 3, 2014

(65) Prior Publication Data

US 2014/0221820 A1    Aug. 7, 2014

Related U.S. Application Data

(60) Provisional application No. 61/760,872, filed on Feb. 5, 2013.

(51) Int. Cl.
  *A61B 90/00* (2016.01)
  *A61B 8/08* (2006.01)
  *A61B 5/06* (2006.01)

(52) U.S. Cl.
  CPC .............. *A61B 8/481* (2013.01); *A61B 5/065* (2013.01); *A61B 8/0841* (2013.01); *A61B 8/488* (2013.01); *A61B 90/39* (2016.02); *A61B 2090/3925* (2016.02)

(58) Field of Classification Search
  None
  See application file for complete search history.

(56) References Cited

U.S. PATENT DOCUMENTS

| | | | | |
|---|---|---|---|---|
| 5,007,721 A | * | 4/1991 | Morris | G02B 26/002 342/6 |
| 5,025,186 A | * | 6/1991 | Tsukada | H02N 2/166 310/323.06 |
| 5,329,927 A | * | 7/1994 | Gardineer | A61B 8/0841 600/439 |
| 6,698,433 B2 | | 3/2004 | Krag | |
| 6,749,554 B1 | | 6/2004 | Snow et al. | |

(Continued)

FOREIGN PATENT DOCUMENTS

WO    WO 2011/154782 A1    12/2011

OTHER PUBLICATIONS

"Needles for Biopsy and Special Purpose," 2011, Cook Medical, pp. 1-2.*

(Continued)

*Primary Examiner* — Tse Chen
*Assistant Examiner* — Nate S Sunwoo
(74) *Attorney, Agent, or Firm* — Woodward, Emhardt, Moriarity, McNett & Henry LLP

(57) ABSTRACT

Devices and methods for enhancing observability under ultrasound imaging of medical devices include temporal markers which are dynamic, producing a variable ultrasound image over time. Included are rotating markers which produce a Doppler shift visible through ultrasound imaging in a Doppler mode and which enhance visibility of the marker. Other devices and methods include alternating streams of fluid contrast agents and saline as well as destroying a fluid contrast agent stream with a high intensity ultrasound pulse.

17 Claims, 3 Drawing Sheets

(56) References Cited

U.S. PATENT DOCUMENTS

| | | |
|---|---|---|
| 6,858,011 B2 | 2/2005 | Schgal |
| 7,235,052 B2 | 6/2007 | Kellar et al. |
| 8,303,509 B2 | 11/2012 | Webler et al. |
| 2002/0065467 A1 | 5/2002 | Schutt |
| 2007/0118333 A1* | 5/2007 | Miyasaka ............... B61F 15/20 |
| | | 702/183 |
| 2009/0131910 A1* | 5/2009 | Webler ................. A61B 8/0841 |
| | | 604/523 |
| 2009/0187103 A1 | 7/2009 | Guracar |
| 2009/0270736 A1* | 10/2009 | Miyamoto ............... A61B 8/12 |
| | | 600/462 |
| 2009/0318746 A1 | 12/2009 | Thurmond, II et al. |
| 2010/0305432 A1 | 12/2010 | Duhay et al. |
| 2011/0130664 A1* | 6/2011 | Nakagawa ............... A61C 1/07 |
| | | 600/459 |
| 2011/0152716 A1 | 6/2011 | Chudzik et al. |
| 2012/0149985 A1* | 6/2012 | Frassica ............. A61B 1/00082 |
| | | 600/137 |
| 2012/0283775 A1 | 11/2012 | Cully et al. |

OTHER PUBLICATIONS

Duffy et al., "The Doppler effect," Mar. 17, 2000, Boston University, http://physics.bu.ed/~duffy/py105/Doppler.html.*
International Search Report and Written Opinion issued in PCT/US2014/014530, dated May 22, 2014.

* cited by examiner

TEMPORAL ECHOGENIC MARKERS

BACKGROUND

The present disclosure relates to echogenically enhanced markers which are used for imaging medical devices within a body.

It is necessary in some medical treatments and applications to place a medical device subcutaneously (e.g. intravascularly) within a body and then subsequently and accurately locate the item within the body. For example, the physician or other user will wish to be able to easily locate the position of catheters or other devices (such as feeding tubes, chest tubes, and drainage tubes) within a body and movable or prone to movement within the body, via transcutaneous ultrasound. Additionally, many medical procedures require precise positioning of medical devices relative to other body parts and organs, such as biopsy procedures for example.

Current procedures can utilize periodic x-rays in order to locate medical devices positioned subcutaneously. However, such procedures can require moving the patient from a bed or room to the x-ray machine. Additionally, x-ray machines can be costly to operate and x-ray procedures are radiation intensive which can cause added complications for a medical patient.

Ultrasound imaging can be used as an alternative to x-ray for imaging medical devices within a body. By applying echogenic markers to medical devices placed within a body, screening processes can be performed bedside by using non-ionizing radiation. This prevents the problems associated with relocating a patient as well as problems associated with extended ionizing radiation exposure which can occur when using x-ray.

However, problems can arise from inherent noise when using ultrasound to image a medical device within a body. When imaging with ultrasound, it can be difficult to precisely locate a medical device especially in relation to body parts and organs due to lack of clarity and/or movement of body parts or ultrasound equipment used in the imaging process. In some cases, echogenic markers (such as echotipping) can increase the echogencity of a medical device. However, these devices can still suffer from problems with image noise and the ability of a physician to differentiate between the medical device and body tissue due to the image noise. Additionally, ultrasound image clarity can be reliant on a physician's ability to precisely position the ultrasound transducer relative to the medical device, which can cause increased difficulty with obtaining useable images.

Thus, there is a need for improvement in the field particularly related to echogenically enhanced medical devices or medical devices having echogenic markers which provide distinctive images which enable physicians to precisely position a medical device within the body relative to other medical devices or body tissue.

SUMMARY

Among other things there are disclosed embodiments of echogenic markers which provide echogenically enhanced imaging visibility for medical devices which are imaged by physicians during ultrasound procedures. In one example, a paddle in the form of a flat rectangular (e.g. planar) plate is mounted to a drive shaft. The drive shaft is driven by a motor or manually, so that the paddle is rotatable about an axis. The rotational motion causes the paddle to turn or spin, and the paddle is of a small size and is able to fit within or on internally-placed devices such as catheters, chest tubes, drainage tubes and the like. During ultrasound procedures, the paddle is caused to rotate about the axis. A Doppler mode of an ultrasound imaging system can be used. While the paddle rotates, one side moves away from the imaging transducer while the other moves towards the imaging transducer. The Doppler shift from the rotating paddle generates an image with varying characteristic properties (i.e. varied intensity, frequency content, phase information, etc., including a single property or any combination of several properties, which creates a "blinking") and/or with colored or contrasting regions corresponding to the paddle sides which are moving towards or away from the imaging transducer.

The rotation rate and direction of rotation can be changed over time in order to alter or enhance the echoing signal. The paddle can be configured with enhanced surfaces that cause a signal scattering in many directions. The enhanced surfaces can include echotipping or other textured surfaces.

In another example, the paddle can be used with an ultrasound imaging system in a normal mode of operation. The paddle rotates such that the image appears on the imaging screen as a blinking image which corresponds to alternating paddle positions in which a flat surface is positioned substantially normal to an imaging transducer projection angle and a position where the paddle has an edge surface positioned substantially normal to the imaging transducer projection angle. In the second position, the paddle reflects less ultrasound energy or does not reflect a distinct signal back to the imaging transducer, while when in the first position the paddle reflects a more energetic or more distinct signal back to the imaging transducer. This variance between the two positions causes a repeating occurrence of a stronger signal and weaker signal, a blinking, to show up on the screen when the paddle is rotating. Motion of the paddle provides a dynamic representation of the location of a device during ultrasound procedures.

Other examples of a marker for dynamic representation under ultrasound can include a wire coiled and/or in a helix shape, attached to a shaft and rotatable. Rotation causes a variability of reflection of ultrasound energy. For example, such variation can be in position (e.g. a reflection or reflection maximum appears to travel along the image) and/or in one or more characteristic properties (e.g. a blinking representation).

The markers described herein can be driven by a torque cable in the case of a medical device such as a catheter where the marker is positioned near the tip of the catheter. A torque cable can run from the marker through the catheter with connection to a motor. Alternatively, the marker can be driven manually. In other examples, a small motor is placed near the tip of the catheter or other medical device such that a torque cable is not needed. Motors can include a small piezoelectric motor or an electromagnetic motor. Motors can be powered with wires extending through the length of the catheter or other medical device. Additionally, the motors may be powered by a battery which is placed near the end of the catheter (or other medical device) which is closest to the user. The battery can also be placed external of the medical device in the case that the motor is located external of the body.

In cases where a battery is used, the battery can be implemented in devices which can be permanently or semi-permanently implanted in a body such as when no external components are needed. The devices can also be used to monitor the inadvertent implantation of surgical gauze or sponges which remain in a body. The marker can be configured such that the battery responds only in the presence of ultrasound energy in order to preserve battery life and extend the useful life of the device. Additionally, the markers can be powered by using the acoustic energy of the power source to spin a paddle or otherwise cause rotation or movement of the marker. These devices would include a piezoelectric element which is excitable by ultrasound and converts mechanical sound wave energy into rotational motion. These types of devices are advantageous over a torque cable configuration or a piezoelectric motor configuration because no external power supply needed. Additionally, the design eliminates concerns about battery life and potential toxicity risk when using a battery.

In another example, a system can include a printed circuit board with or within a medical device which shifts or alters a received ultrasound frequency and transmits an altered ultrasound frequency. In this type of device, a printed circuit board contains a receiving piezoelectric element which converts the energy of ultrasonic waves into electrical signals which serve as a power source and a frequency reference. The electrical signals are fed through a frequency shift circuit and into a transmitting piezoelectric element, which emits ultrasonic waves at the shifted frequency to the transducer. The system can be powered by a battery.

In another example, a fluid contrast agent can be used in a catheter or other implantable medical device to enhance observability. The fluid contrast agent can include microbubbles. In one example, an alternating stream of fluid contrast agent and saline can be pumped down a catheter. The alternating stream will cause a blinking or flashing image on an ultrasound image screen since the materials reflect ultrasound differently, to enable the physician to more quickly and accurately locate the medical device. Another example includes a catheter or other medical device with a plurality of lumens extending through walls in which an alternating stream of fluid contrast agent and saline can be pumped through. In another example, a steady steam of fluid contrast agent can be pumped through a medical device and then the microbubbles can be periodically destroyed with a high intensity ultrasound pulse. The high intensity ultrasound pulse will destroy momentarily the reflective capabilities of the microbubbles within the fluid contrast agent. This destruction changes the reflective nature of a portion of the device at a given location, and when done periodically creates a dynamic change in the image on the screen (e.g. a blinking or flashing on and/or off).

Another example can include a medical device configured with echogenic enhancements such as echotipping or dimples or other types of textured surfaces. The medical device can have a shaft that is configured with a series of echogenically enhanced regions on an outer surface. The shaft is translationally movable within another medical device such as a cannula wherein the cannula is echoreflective. A physician manually moves the shaft having echogenically enhanced regions within the cannula such that the echogenically enhanced regions are alternatingly visible or reactive to a signal from an ultrasound transducer. When the enhanced ultrasound region is within the echo reflective tube, the enhanced region will be blocked from reflecting the signal. When the shaft is moved out of the tube it is not blocked from reflecting a signal. This movement will cause a change of reflective condition(s) and a dynamic image change such as a blinking or flashing on the ultrasound imaging screen. In this situation the physician can manually move the medical device relative to the cannula or it can alternatively be moved mechanically by a motor.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
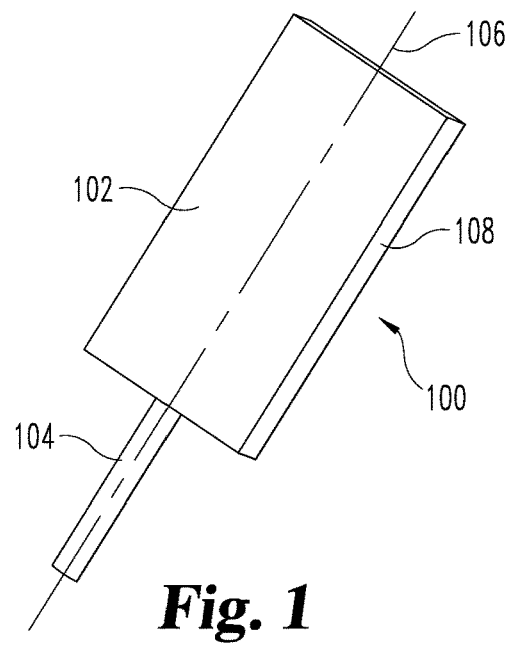
FIG. 1 is a perspective view of an embodiment of a rotating echogenic marker.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates.

FIG. 1 depicts an echogenic marker 100. The marker 100 is used for enhancing an ultrasound image of a device which is placed subcutaneously in a body. The marker 100 is generally small enough to fit within catheters, chest tubes, drainage tubes or other medical devices which are inserted subcutaneously.

The marker 100 includes a paddle 102. The paddle 102 is depicted in this embodiment as a generally flat planar object, for example of substantially rectangular shape. The paddle 102 could also be constructed in a variety of different shapes such as circular or oval, for example. Additionally, the paddle 102 need not be a flat planar object; the paddle 102 could be any of a variety of shapes as described below. The paddle 102 is connected to a shaft 104. The shaft 104 and paddle 102 are rotatable about an axis 106. The shaft 104 can be driven rotatably manually or by a motor. In particular examples, paddle 102 is constructed of stainless steel or another material having acoustic impedance much greater or much less than water or other tissues and fluids within a body.

Generally an ultrasound signal is partially reflected at the interface of two mediums having different acoustic impedances such as water and the surface of the paddle 102. Because the paddle 102 is constructed of stainless steel or other material having acoustic impedance different than water, the paddle 102 will reflect partially an ultrasound signal when positioned within a substance such as water. During ultrasound procedures, a transducer emits an ultrasound signal and the signal is reflected partially as it encounters changes in medium. A portion of the reflected signal returns to a transducer and from there the signal is processed to create an image viewable by a physician. The characteristic ability of an object to reflect ultrasound waves is described herein as "echogenicity". The term "echolucent" is used herein to describe a characteristic of an object, wherein that object generally reflects less ultrasonic signal in comparison to a second object in the context of a particular environment. In other words, "echolucency" describes the characteristic of having less acoustic attenuation in comparison to something else in a particular environment.

Figure 5:
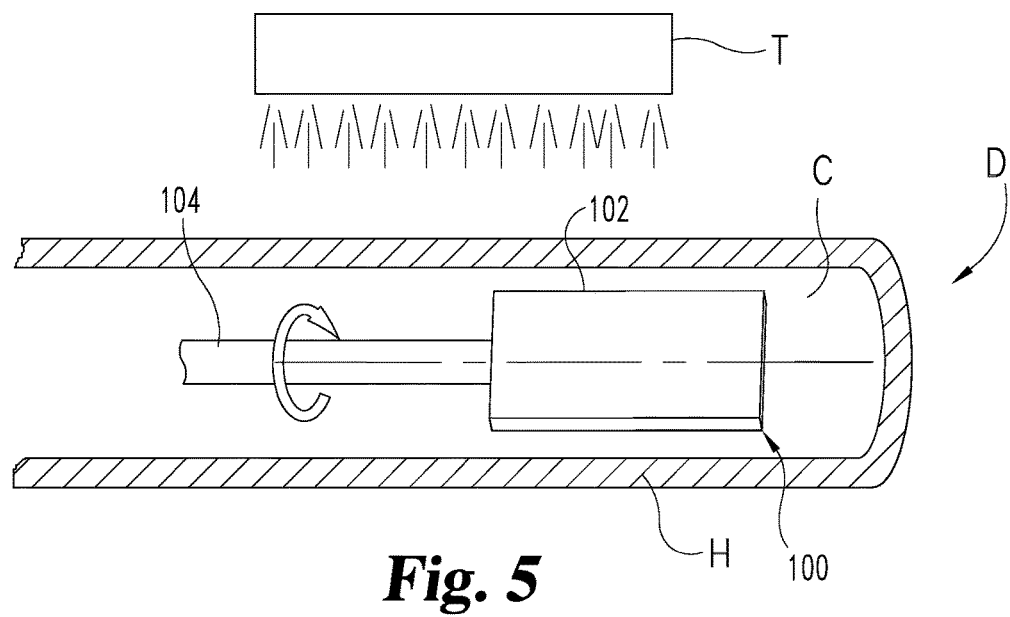
FIG. 5 is a part cross-sectional view of an embodiment of a device including an embodiment of a dynamic marker as in FIG. 1, with a schematic representation of an ultrasound transducer.

The marker 100 is preferably fitted in a medical device D (FIG. 5), e.g. a catheter. This embodiment of device D has a housing H which is wholly or partially echolucent relative to body tissue, defining a chamber C in which at least part of marker 100 is placed. The housing can be constructed of a variety of polymers or other materials which have acoustic impedance similar to water and body tissue. In that way, the housing is echolucent when positioned within a body such that signal reflections from the marker 100 are not blocked or hidden by the housing.

The marker 100 can be used in conjunction with Doppler ultrasound. Doppler ultrasound is an imaging modality that looks for a frequency shift in echoes to determine the relative motion of an object. A Doppler marker is a marker that returns a frequency shifted version of the transmitted ultrasound pulse. Many modern ultrasound consoles have an ultrasound Doppler mode in which Doppler signals are superimposed in color on top of grey scale anatomical images. The Doppler mode can be used in conjunction with the marker 100 and other embodiments described herein.

A mechanical frequency shift can be achieved with the paddle 102. During operation, the paddle is rotated on the shaft 104 about the axis 106. An imaging system including an ultrasound imaging transducer T emits an ultrasound signal directed at medical device D having the marker 100 with the rotating paddle 102. In most orientations, one side of the paddle 102 moves away from the transducer while the other side moves towards the transducer. The ultrasound signal should be minimally reflected at the surfaces of the medical device which are echolucent, such as for example the housing H. However, the ultrasound signal is reflected when it encounters paddle 102 and its material acoustically different from the surrounding medical device and body tissue. The motion of the paddle 102, with a first portion offset to one side of shaft 104 moving generally or roughly toward the imaging transducer and a second portion offset to the other side of shaft 104 moving generally or roughly away from the imaging transducer, causes a Doppler frequency shift in the portion of the ultrasound signal which is reflected back to the transducer. That is, one side of paddle 102 (moving toward the transducer) reflects a signal having a frequency higher than the emitted signal and the other side (moving away from the transducer) reflects a signal having a frequency lower than the emitted signal. When using a Doppler mode in an ultrasonic imaging system, the rotating motion of the paddle 102 will thus cause one side of the paddle 102 to appear blue or bluer in the image and the other side to appear red or redder (or whichever distinguishing contrasts, colors or patterns the ultrasound system is configured to display). The contrast of the red and blue image portion representing the paddle 102 relative to any other motion or other signals within the body creates a distinct and readily identifiable image during the imaging process. In that way, a physician can more readily and easily locate the position of the marker 100 within a body relative to various parts of the body and also various parts of the imaging system and marker 100.

The marker 100 can produce an even higher differentiation from surrounding tissue by varying the rate of revolution of paddle 102 over time. By changing the revolution rate over time, the echoed ultrasound signal can be even further varied from the originating signal, such that the image can be further distinguished from the surrounding tissue and other parts of the medical device. Additionally, a higher differentiation can be achieved by periodically or frequently changing the direction of rotation. A change in the direction of rotation of paddle 102 will produce a change in the viewed image such that red and blue will alternate in the image in a blinking fashion. The blinking serves to further enhance the visibility of the marker 100.

Figure 2:
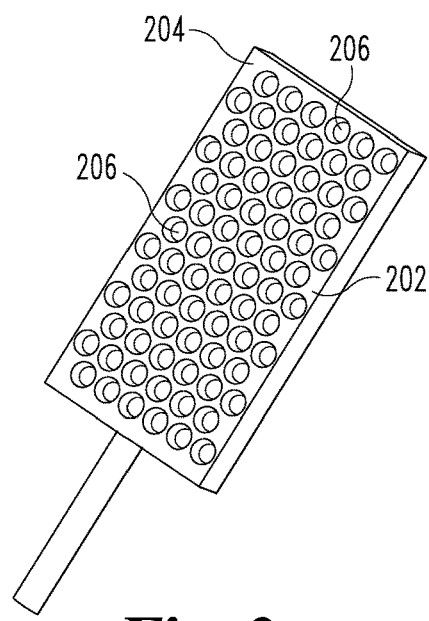
FIG. 2 is a perspective view of an alternative embodiment of the FIG. 1 marker having echogenic enhancements.

It is beneficial for the paddle 102 to have surfaces that cause a signal scattering in many directions. An example of a marker 200 constructed to cause a signal scattering is shown in FIG. 2. FIG. 2 shows an embodiment of a paddle 202 that has a dimpled surface 204 with a series of dimples 206 and an opposite-facing flat or smooth surface. Alternatively, dimples 206 can be located on multiple surfaces of the paddle 202. The dimples 206 can be any of a variety of echogenically enhancing features which are positioned on the surface of an object. In the FIG. 2 example, the dimples 206 are generally a series of concave depressions which, when viewed at a cross-section, resemble truncated half-hemispheres with flat-bottomed or round-bottomed surfaces. In other embodiments, dimples 206 can be a variety of geometric configurations or other echogenic enhancements, such as, for example, small cavities which are machined into the surface, divots, grooves, lines, ridges, or rough texturing. The dimples 206 can be individually located on a surface of the paddle 202 such that the dimples 206 are not in communication with each other or do not touch each other and are simply a series of individual geometric configurations. Alternatively, the dimples 206 could be machined or etched into the dimpled surface 204 or created in such a way to create a texture in the dimpled surface 204.

In practice during ultrasound procedures, the dimples 206 or other echogenic enhancements scatter an ultrasound signal such that the wave is reflected in a variety of directions. This reflection surface varies from a smooth surface from which ultrasound is reflected primarily in one direction only in which the direction is directly dependant on the relationship between the directional vector of the emitted signal and the normal plane of the reflection surface. In the case of a smooth surface, the reflection surface should be positioned primarily normal to the directional vector of the emitted signal in order for the reflected signal to reflect back to the receiving transducer. In the case of a rotating smooth surface, the quality of the imagable signal depends on the relative positions between the transducer and the rotating surfaces. An imagable signal is available only when the rotation angle provides alignment between the emitted signal directional vector and the surface normal of the reflecting surface. Typically, the imagable signal corresponds with a relatively small angular range. In contrast, when imaging a marker having an echogenically-enhanced surface, such as with the dimples 206, an imagable signal is available for a much wider angular range due to the scattering of the ultrasound signal upon interacting with the dimples 206. In this way, the dimples 206 of the paddle 202 allow the paddle to be more easily imaged during ultrasound procedures without needing to ensure that the paddle and the imaging transducer are positioned precisely in order to obtain an image.

An additional functionality of the markers can include physically moving a marker during imaging so that the marker differentiates from surrounding tissue by having a changing echo reflectivity with time. Because body tissue has a time constant echo reflectivity, a marker can be distinguished by observing sequential imaging frames and monitoring for a location with a changing luminosity, or blinking. In other words, a blinking can be achieved by having a marker with a portion which moves into and out of an imaging plane. Alternatively, a blinking can be achieved by having a marker capable of two or more states in which the marker reflects an amount of ultrasonic energy which is different in each state. Alternatively, a blinking can be achieved by providing a point of reflection which moves or changes location spatially with time.

Body tissue may move periodically with the cardiac and respiration cycles at approximately 0.2 Hz and 1.3 Hz respectively. It is desirable that the blinking have a frequency that does not overlap with either of these frequencies especially when imaging in or near the thoracic cavity.

In use of the embodiment of paddle 102 in an ultrasound-monitored procedure, paddle 102 is rotated. The rotation rate can be set according to the desired blink frequency and can be provided by a mechanical motor or manually by a physician or other technician. When the shaft 104 is rotated the paddle 102 rotates with it. At a time during rotation when the flat planar surface of the paddle 102 is directed towards the ultrasonic transducer, a relatively large portion of ultrasound waves reflected to the transducer and an image is produced in the imaging system. As the paddle 102 is rotated to a configuration such that an edge 108 of the paddle 102 is facing the transducer, a significantly smaller portion of ultrasound waves are reflected to the transducer and a different image is produced in the imaging system. As the paddle 102 is further rotated, a flat planar surface of the paddle will once again reflect towards the ultrasound transducer again changing the ultrasound image. In this way, a physician can observe dynamic changes in intensity in an ultrasound image, i.e. a flashing or blinking point or area. If the blinking portion blinks at a rate synchronous to the rotation rate of the paddle 102, the physician can be confident that the blinking portion represents the position of the medical device.

The paddle 102 can be configured with echogenic enhancements as mentioned previously and as shown and discussed in FIG. 2. These enhancements allow more tolerance in the angle which the ultrasound transducer must be positioned relative to the paddle 102. The paddle 202 could also have regions including ultrasound absorbers which are distinct from echogenic enhancements. Ultrasound absorbers are materials or techniques which cause an object to become more echolucent with respect to its environment. The distinct regions can be alternating so as to further increase the contrast of the visual blinking which is observable by the physician.

Figure 3:
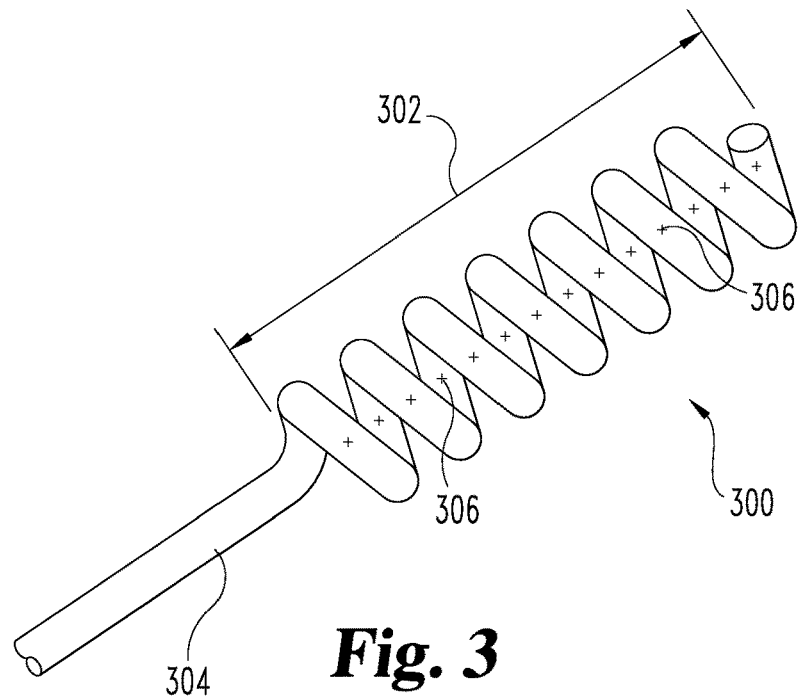
FIG. 3 is a perspective view of an embodiment of a rotating echogenic marker.

The markers described herein are not limited to a flat planar paddle but rather could be constructed of a variety of shapes and sizes. In other embodiments, a paddle 102, 202 could be oval or egg-shaped, spherical, substantially cubic or another rectangular solid, or a helical shape with a central axis coincident with or alongside an axis of shaft 104. For example, a marker could be constructed as a coiled section of a wire. An embodiment of a helix-shaped marker 300 is shown in FIG. 3. The marker 300 includes a coiled portion 302 which is fixed to a shaft 304. The coiled portion 302 can be integral to the shaft or alternatively the coiled portion 302 can be a separate part which is attached to the shaft 304. The coiled portion 302 is positioned coaxial with a central axis of the shaft 304 such that when the shaft 304 rotates, the coiled portion 302 simultaneously rotates with the shaft 304. The coiled portion 302 is constructed of a metal or other material having acoustic impedance different from water so that it reflects ultrasound when positioned within a body. The coiled portion 302 can be constructed by forming a wire into a helix shape as one example.

With respect to an imaging transducer, the coiled portion 302 has specular highlights 306 which are points on the surface of the coiled portion 302 that have a surface normal which is aligned with the viewing angle of the transducer. The specular highlights 306 represent a point of reflection which will reflect back to the transducer. The position of the specular highlights 306 will change depending on the location of the transducer relative to the marker 300 and on rotation of coil 302. When the shaft 304 and coiled portion 302 are rotating and the marker 300 is being imaged with an ultrasound imaging system, the specular highlights 306 will appear to move in an axial direction either towards the shaft 304 or away from the shaft 304 depending on the direction of rotation. The motion of the specular highlights 306 will cause a blinking or flashing to appear in the ultrasound image. The rotation rate of the shaft 304 can be configured to be in a relation with the diameter of the coils located in the coiled portion 302 such that the specular highlights appear to alternate from one position to another position and back to the original position such that this movement is what indicates the blinking in the ultrasound image.

As mentioned previously, the markers described herein can be used in a variety of medical devices. As one example, the marker can be used in a catheter or other medical device which has a portion having an end and a middle portion which extends from within the body externally to the outside of the body. In such a configuration, a rotating motion can be imparted through use of a torque cable positioned within the catheter. The torque cable can be connected to an external motor or alternatively the torque cable can be driven manually by the physician. Additionally, the rotation of the marker could be driven by a small motor embedded inside the catheter. If the motor is embedded inside the catheter, the motor can be one of a variety of suitable motors. For example, the motor could be an electromagnetic motor or alternatively, it could be a piezoelectric motor. Piezoelectric motors may be preferable due to their smaller size than electromagnetic motors. More specifically, a piezoelectric motor with a diameter of 0.3 mm to 4 mm can be used in this context. The piezoelectric motor could be located relatively close to the marker. This helps to avoid problems that can be caused by torque cables which must generally be housed in the dedicated lumen and have a relatively large bend radius. Torque cables can prevent catheters and other devices from being routed through and around certain system component devices and certain portions of the body.

If a motor is positioned relatively close to the marker and a medical device, it can be powered in several ways. One way is to extend wires throughout the length of the catheter from the marker to an external power source. Alternatively, the motor can be powered by a battery. Battery power is particularly useful for medical devices which are placed subcutaneously for extended periods of time with no consistent external access such as in the case of a catheter. A battery powered motor is particularly useful in implanted devices because no external components are needed. This is useful, for example, to monitor inadvertent implantation of surgical gauze or sponges as well as other medical devices which are placed in a permanent or semi-permanent fashion in a body. In that case, markers could be placed within the gauze or sponge and then later positively identified prior to extraction from the body.

For extended use of the medical device, the battery life can be preserved by implementing a system whereby the battery only discharges in the presence of ultrasound energy. In that case, when an ultrasound signal is applied to the area of the medical device, the ultrasound waves would interact with a sensor. The sensor would trigger a switch which engages the battery and causes motion of the marker. In this way, the battery and motor can rest in a non-active state and conserve battery power until such time as it is necessary to activate and engage the motor and rotate a marker during an ultrasound procedure. The sensor can be a piezoelectric element or other suitable device which can accept and sense ultrasound waves.

An alternative example can be used as a source of mechanical rotation in place of a battery. The marker can be rotated by a microelectromechanical device having an element which is excitable by ultrasound, such as a piezoelectric element. This device would store energy and use it to power the motor which rotates the paddle or otherwise causes motion of the marker. The microelectromechanical device can include a piezoelectric element which is able to receive sound waves and convert the mechanical action of the sound wave into a rotating action which engages the shaft of the marker and causes it to rotate. That energy could alternatively be stored and used to power a motor which, in turn, rotates the marker. The rotation rate is set at a frequency much lower than that of the ultrasound signal. This design can be advantageous over the use of a torque cable because it does not require an external power supply. This design can be used in implantable devices as described above. Additionally, there is no concern about battery life as the device is perpetually energized by an ultrasound signal. Additionally, this can eliminate any concern about toxicity from a battery being positioned within a body when a battery is not incorporated in the design.

Another alternative example of an enhanced echogenic marker can include a printed circuit board having an active piezoelectric element, a frequency shift circuit and a piezoelectric transmitter all mounted on the small printed circuit board. The circuit board can work in conjunction with the Doppler mode of an ultrasound system by converting a frequency obtained from an imaging transducer and retransmitting an altered frequency that can be sensed and imaged by an ultrasound system using Doppler mode. The device includes a receiving piezoelectric element which converts mechanical ultrasound energy into electrical signals that serve as a power source and a reference frequency. The electrical signals are fed through a frequency shift circuit (similar to an FM radio transmitter) and into the transmitting piezoelectric element. The transmitting piezoelectric element then transmits a shifted frequency signal back to the receiving transducer of the imaging system. Such a device could be powered with a battery or alternatively could be powered externally in any of the ways discussed previously.

Figure 4:
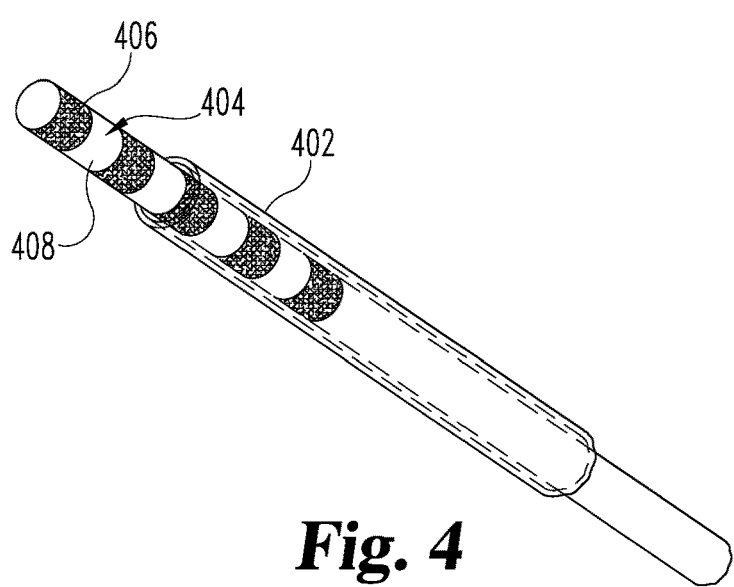
FIG. 4 is a perspective view of an axially-movable echogenic marker.

An additional alternative example of an echogenically enhanced ultrasound marker includes a marker having echogenic enhancements which are movable into and out of an imaging plane. An example of this is shown in FIG. 4. FIG. 4 has a cannula 402 which contains a lumen. Positioned within the lumen is a shaft 404. The shaft 404 is axially and translatably movable within the cannula 402. The shaft 404 contains echogenic regions 406 and non-echogenic regions 408. The echogenic regions 406 can include textured or dimpled portions such as those previously described or any of a variety of known echogenic enhancements which can be placed on a medical device. The cannula 402 can be constructed of a metal or other material having a high echogenicity compared to water or tissue or other items located within a body. The shaft 404 can be moved axially within the cannula manually by the physician. Alternatively, it could be movable by a motor mounted within the medical device or alternatively external of the medical device in the case of a medical device such as a cannula which has a portion located within the body as well as external to the body.

During an ultrasound imaging procedure, a physician can observe the ultrasound image and then engage movement of the shaft 404 either manually or through a motor as previously discussed. The movement can also be automatically engageable such as through use of a controller. As the echogenic regions 406 move external to the cannula 402, a reflection will occur where previously no reflection occurred. A physician can watch for reflections to appear at a frequency relative to that of the motion of the frequency of axial translation of the shaft. In this way a blinking or flashing portion can be identified and the physician can equate that blinking portion with the location of the inserted medical device.

Another example of an echogenically enhanced marker includes use of a fluid contrast agent. The fluid contrast agent can be in the form of contrast agents having microbubbles to reflect ultrasound. The microbubbles generally have a shell which contains a gas core. The shell can be constructed of a material having suitable mechanical elasticity as well as acoustic impedance similar to that of body tissue such as various types of polymers or albumin, galactose, or lipid, as well as other types of materials. When the microbubbles interact with an ultrasonic sound wave, they compress, oscillate and reflect a characteristic echo. The gas core can be composed of air or other gases.

Figure 6:
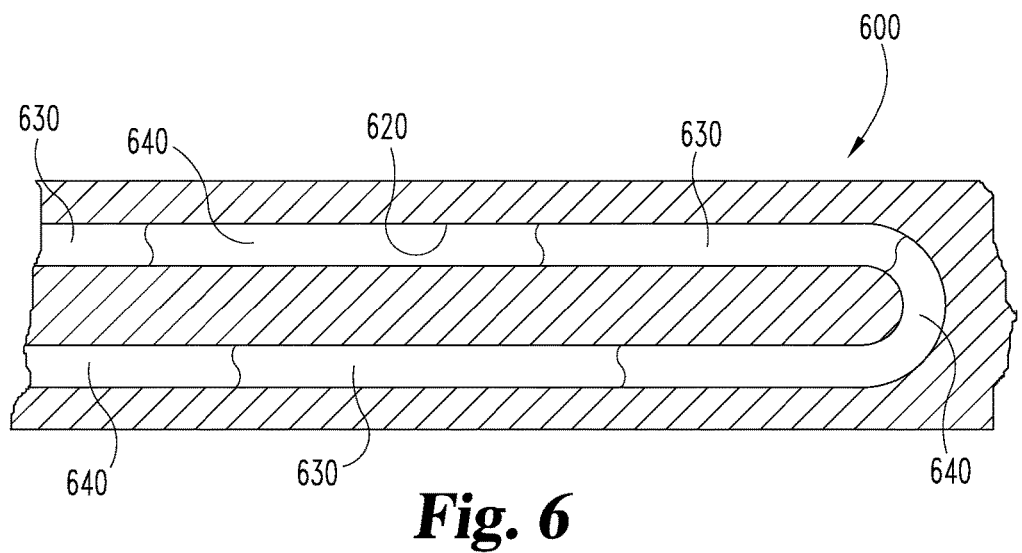
FIG. 6 is a part cross-sectional view of an embodiment of a device adapted to have dynamic echogenic properties.

In the context of enhanced echogenic markers and medical devices, the fluid contrasting agent can be used in conjunction with a medical device 600 (FIG. 6) such as a catheter which has a portion inserted into a body as well as a portion extending externally from the body. The embodiment of FIG. 6 includes a lumen 620 as a closed loop running through the catheter. The catheter can contain a central lumen or alternatively it can contain one or a series of lumens positioned within the wall of the catheter. The lumen is fluidly connected to at least two sources, one containing a fluid contrast agent 630 and the other containing saline or other substantially echolucent fluid 640. A stream of fluid contrast agent 630 can be applied to the lumen of the catheter or other medical device. The stream can be interrupted by applying a stream of saline 640 into the lumen. The stream of saline 640 can subsequently be interrupted by applying a stream of fluid contrast agent 630 to the lumen. The alternating streams can continue in this way, to provide alternating portions of lumen 620 respectively filled with echogenic fluid and echolucent fluid. The lumen can discharge into a common reservoir which could contain both fluid contrast agent and saline. In this way, alternating streams of fluid contrast agent and saline can be applied to the lumen.

During ultrasound imaging procedure when imaging the catheter, a physician can visually locate the catheter by identifying the characteristic blink from the alternating streams of fluid contrast agent and saline. When the fluid contrast agent is applied to the catheter during an ultrasound imaging procedure, the ultrasound signal will reflect off of the micro-bubbles or other agents located within the fluid contrast agent and produce a distinctive signal in the image. When that fluid contrast agent is replaced with saline, the distinctive image will change or disappear from the ultrasound image. By alternating between the saline and the fluid contrast agent, a physician can identify a portion of the image where a blink or flashing area occurs at a frequency in relation to the frequency of the alternating stream through the catheter. This gives the physician knowledge of the catheter's position within the body so as to assure that the medical device or catheter is being accurately located. This is useful during ultrasonic imaging procedures whereby a physician can view an image and identify a blinking portion wherein the blinking portion is due to the alternating streams of fluid contrast agent in saline.

An additional example applies a steady stream of fluid contrast agent through a catheter (e.g. device 600) particularly through one or more lumens (e.g. 620) located within the walls of the catheter or a central lumen located within the catheter, similar to the catheter described above. During an ultrasound procedure, the steady stream of fluid contrast agent can be periodically subjected to a high intensity ultrasound pulse to destroy or alter some or all of the microbubbles in a given area, so as to change or eliminate the reflectivity of the contrast agent in the given area. Subsequently, and between pulses of high intensity ultrasound, the stream can be repopulated with fluid contrast agent having unaffected microbubbles. In a similar manner as described above, a physician can observe an ultrasound image and identify a location of the ultrasound image that changes at a frequency relative to the frequency of a high intensity ultrasound pulse. In this way, the location of the catheter or other medical device can be ascertained by the physician.

The descriptions and examples described above are not limited to the specific details described herein. For example, the movement is not limited to rotational or translational movement and other types of movement could be appropriate such as vibration. Similarly, the materials used to construct the various examples can be a variety of different materials. For example, the markers can in some cases be constructed of stainless steel and in other cases can be constructed of ceramics or other materials having acoustic impedance much greater or much less than that of water or human body tissue.

The examples described herein are not limited to any specific applications described. For example, the various markers could be used with catheters or biopsy needles or any of a variety of objects which are placed in the body and which are needed to be imaged during an ultrasound procedure either permanently or temporarily. It should be noted that the examples described above include details of components and methods of use which are interchangeable with one another. For example, the FIG. 4 example can in some cases be used with the Doppler mode imaging procedures. The FIG. 3 example could be used in some cases with the Doppler imaging procedures. Additionally, the FIG. 3 example could be used with the temporal marker imaging procedures as described above. In this way, a variety of echogenically enhanced markers are described which can be used with a variety of different methods to more accurately and with a greater degree of certainty position and locate medical devices within a body.

While the disclosure has been illustrated and described in detail in the drawings and foregoing description, the same is to be considered as illustrative and not restrictive in character, it being understood that only the preferred embodiment has been shown and described and that all changes, equivalents, and modifications that come within the spirit of the following claims are desired to be protected. Features described with respect to a particular embodiment may be used with or incorporated in other embodiments. All publications, patents, and patent applications cited in this specification are herein incorporated by reference as if each individual publication, patent, or patent application were specifically and individually indicated to be incorporated by reference and set forth in its entirety herein.

What is claimed is:

1. A medical device for use with an ultrasound imaging system configured to process ultrasound signals and display images in ultrasound procedures comprising:
    a marker which is capable of reflecting ultrasound waves;
    wherein the marker is movable about an axis of rotation between a first position and a second position;
    wherein the marker further includes a first portion configured to reflect a first ultrasound wave back to an ultrasound wave source and a second portion configured to reflect a second ultrasound wave back to the ultrasound wave source and wherein said first portion is offset to one side of said axis of rotation and said second portion is offset to the other side of said axis of rotation; wherein the marker further includes echogenic enhancements located on surfaces of the marker, whereby when an ultrasound signal is applied to the marker the echogenic enhancements cause a scattering of the ultrasound waves; and,
    wherein when said marker moves between said first position and said second position, said first portion of the marker moves towards the ultrasound wave source, while said second portion of the marker moves away from the ultrasound wave source, whereby when the medical device is placed within a body and viewed on the ultrasound imaging system during ultrasound imaging procedures, the first and second portions of the marker concurrently reflect a portion of the ultrasound waves back to the ultrasound wave source, and whereby the ultrasound waves reflected from the first portion have a higher frequency than the ultrasound waves reflected from the second portion.

2. The medical device of claim 1, wherein said marker is rotatable about the axis of rotation at a first rotation rate; and
    wherein when positioned within a body and when rotating at the first rotation rate the marker produces a Doppler shift which is observable through ultrasound imaging procedures when the marker is subjected to ultrasound waves.

3. The medical device of claim 2, wherein the medical device is configured to be implanted within a human body.

4. The medical device of claim 2, further comprising a battery and an ultrasound sensor, wherein rotation of the marker is powered by the battery, wherein the medical device is switchable between an active state and an inactive state, wherein when in the active state the marker rotates and when in the inactive state the marker does not rotate, and wherein subjecting the ultrasound sensor to ultrasound waves changes the medical device from the inactive state to the active state.

5. The medical device of claim 2, wherein rotation of said marker causes the first portion of the marker to appear as a first color on the ultrasound imaging system, and causes the second portion of the marker to appear as a second color on the ultrasound imaging system.

6. The medical device of claim 2, wherein the direction of rotation of the marker is periodically changeable over time.

7. The medical device of claim 1, wherein when the marker is placed within a body and viewed on an ultrasound image during ultrasound imaging procedures, sequential movements of the marker between the first position and the second position cause a blink on the ultrasound image.

8. The medical device of claim 1, wherein the marker further comprises echogenic enhancements located on surfaces of the marker, whereby when ultrasound waves are applied to the marker the echogenic enhancements cause a scattering of the ultrasound waves.

9. The medical device of claim 8, wherein said echogenic enhancements comprise concave depressions located on the surface of the marker.

10. The medical device of claim 1, further comprising a battery and an ultrasound sensor, wherein rotation of the marker is powered by the battery, wherein the medical device is switchable between an active state and an inactive state, wherein when in the active state the marker rotates and when in the inactive state the marker does not rotate, and wherein subjecting the ultrasound sensor to ultrasound waves changes the medical device from the inactive state to the active state.

11. The medical device of claim 1, wherein the marker is a flat, planar shaped object rotatably fixed to a shaft having a shaft axis which is coaxial with the rotation axis.

12. The medical device of claim 1, wherein the marker is a helix shaped object fixed to a shaft having a shaft axis which is coaxial with the rotation axis.

13. The medical device of claim 1, wherein the medical device is configured to be implanted within a human body.

14. The medical device of claim 1, wherein the marker is rotatable about the axis of rotation at a variable rotation rate.

15. The medical device of claim 1, wherein the marker further comprises ultrasound absorbers located on surfaces of the marker, and wherein the ultrasound absorbers cause said marker to become more echolucent at the surfaces where the ultrasound absorbers are present.

16. A medical device for use with ultrasound procedures comprising:
  a marker which is capable of reflecting ultrasound waves;
  wherein the marker is movable about an axis of rotation between a first position and a second position;
  wherein the marker further includes a first portion configured to reflect ultrasound waves back to an ultrasound wave source and a second portion configured to reflect ultrasound waves back to the ultrasound wave source and wherein said first portion is offset to one side of said axis of rotation and said second portion is offset to the other side of said axis of rotation; wherein the marker further includes echogenic enhancements located on surfaces of the marker, whereby when an ultrasound signal is applied to the marker the echogenic enhancements cause a scattering of the ultrasound waves; and,
  wherein when said marker moves between said first position and said second position, said first portion of the marker moves towards the ultrasound wave source, while said second portion of the marker moves away from the ultrasound wave source, whereby when the medical device is placed within a body and viewed on an ultrasound image during ultrasound imaging procedures, the first and second portions of the marker concurrently reflect a portion of the ultrasound waves back to the ultrasound wave source, and whereby the ultrasound waves reflected from the first portion have a higher frequency than the ultrasound waves reflected from the second portion; and,
  wherein the medical device includes a converter which includes a piezoelectric element excitable by ultrasound waves, wherein the converter converts ultrasound wave energy into rotational energy, whereby when the medical device is placed within a body and viewed on an ultrasound image during ultrasound imaging procedures, application of ultrasound waves to the medical device causes the marker to rotate about the axis of rotation.

17. The medical device of claim 16, wherein said marker is rotatable about an axis at a first rotation rate; and
  wherein when positioned within a body and when rotating at the first rotation rate the marker produces a Doppler shift which is observable through ultrasound imaging procedures when the marker is subjected to ultrasound waves.

* * * * *